United States Patent [19]

Beck et al.

[11] Patent Number: 5,021,274

[45] Date of Patent: Jun. 4, 1991

[54] DETACHABLE COUPON FOR LAMINATED CORRUGATED PACKAGING MATERIAL AND METHOD OF MANUFACTURE

[75] Inventors: Louis B. Beck; Joseph C. Beck, both of Little Rock, Ark.

[73] Assignee: Union Camp Corporation, Wayne, N.J.

[21] Appl. No.: 280,302

[22] Filed: Dec. 5, 1988

[51] Int. Cl.⁵ ...................... A61F 13/02; B65D 73/00; G09F 3/00

[52] U.S. Cl. ...................................... 428/41; 428/182; 428/352; 428/354; 428/211; 428/43; 428/136; 428/138; 428/195; 206/459; 206/831; 283/81; 283/101; 283/103; 283/105; 40/312; 229/100; 229/118; 229/4.5; 493/53; 493/54; 493/961

[58] Field of Search ............... 493/210, 220, 224, 961, 493/53, 54; 428/182, 184, 40, 41, 42, 343, 352, 43, 136, 138, 195, 211; 206/459, 831; 283/81, 101, 103, 104, 105; 281/34; 40/310, 312; 229/100, 118, 4, 5, 110; 483/53, 54

[56] References Cited

U.S. PATENT DOCUMENTS

| | | | |
|---|---|---|---|
| Re. 24,962 | 4/1961 | Loderhose . | |
| 686,038 | 11/1901 | Edgar et al. . | |
| 1,004,055 | 9/1911 | Martin et al. . | |
| 2,142,370 | 1/1939 | Claff . | |
| 2,420,045 | 5/1947 | Krug . | |
| 3,110,121 | 11/1963 | Corrinet . | |
| 3,463,303 | 8/1969 | Gorman et al. . | |
| 3,914,483 | 10/1975 | Stipek, Jr. . | |
| 3,958,744 | 5/1976 | Herglotz . | |
| 4,308,679 | 1/1982 | Ray et al. | 40/312 |
| 4,318,235 | 3/1982 | Augeri . | |
| 4,345,393 | 8/1982 | Price et al. | 206/831 |
| 4,379,573 | 4/1983 | Lomeli et al. . | |
| 4,519,631 | 5/1985 | Stone et al. . | |
| 4,549,750 | 10/1985 | Stone et al. . | |
| 4,767,654 | 8/1988 | Riggsbee | 428/42 |

FOREIGN PATENT DOCUMENTS

| | | | |
|---|---|---|---|
| 2047860 | of 1971 | Fed. Rep. of Germany | 206/831 |

*Primary Examiner*—Ellis P. Robinson
*Assistant Examiner*—Donald J. Loney
*Attorney, Agent, or Firm*—Edward J. Sites

[57] ABSTRACT

Laminated packaging material includes a corrugated inner ply, a paperboard outer ply having a detachable coupon portion outlined with a perforated die cut, an adhesive between facing surfaces of the outer ply and the corrugated inner ply for adhering the facing surfaces to one another, and an adhesion-preventing agent on the detachable coupon portion of the facing surface of the outer ply for preventing adhesion of the detachable coupon portion to the corrugated inner ply. The laminated packaging material may be manufactured according to a first sequence of steps wherein the adhesion preventing agent is applied to the detachable coupon before the detachable coupon is outlined with a perforated die cut, and the adhesive is applied only to the corrugated inner ply. Alternatively, the laminated packaging material may be manufactured in accordance with a second sequence of steps wherein the detachable coupon portion is first outlined with a perforated die cut, the adhesion-preventing agent is subsequently applied to the detachable coupon portion, and the adhesive is subsequently applied to at least one of a facing surface of the corrugated inner ply and a facing surface of the paperboard outer ply which includes the adhesion-preventing agent. A long slot and/or a tab may be provided along one edge of the detachable coupon to facilitate removal of the coupon.

10 Claims, 4 Drawing Sheets

DETACHABLE COUPON FOR LAMINATED CORRUGATED PACKAGING MATERIAL AND METHOD OF MANUFACTURE

BACKGROUND OF THE INVENTION

The present invention relates to detachable coupons for laminated packaging material, and more particularly to a detachable coupon for laminated packaging material with a corrugated substrate.

It has become common place to provide redeemable coupons along with packaged merchandise. Such merchandise coupons may be provided in a number of ways. First, the coupon may be enclosed within the merchandise package. Second, the coupon may be releasably affixed to the exterior surface of the merchandise package. Third, the coupon may be printed on the exterior surface of the merchandise package.

Enclosing the coupon within the merchandise package carries with it the attendant disadvantage that the coupon cannot be redeemed until the merchandise package is opened. Releasably affixing the coupon to the exterior surface of the merchandise package carries with it the attendant disadvantage that the coupon is often lost or stolen during handling of the merchandise package prior to sale. Printing the coupon on the exterior surface of the merchandise package carries with it the attendant disadvantage that the coupon must be removed with a knife or scissors, thereby destroying the integrity of the merchandise package.

Attempts have been made to provide coupons of the third type which may be removed without destroying the integrity of the packaging material. One such method for laminated packaging material is disclosed in U.S. Pat. No. 4,345,393. As there disclosed, the exterior surface of a glossy finish paper outer ply is imprinted with the desired package printing material including a redeemable coupon, a release agent or adhesive-repellant medium is imprinted on the rear surface of the coupon portion of the outer ply, and the outer ply is laminated to a relatively rigid paperboard or cardboard inner ply by means of an intervening adhesive layer. Subsequent to lamination, a tear outline defining the coupon area is cut through the outer ply, release agent and adhesive layer to provide for removal of the coupon without damage to the inner ply of the packaging material. A similar method without use of the release agent or adhesive-repellant medium is also disclosed for packaging material comprised of a laminated inner ply.

Although the method disclosed in U.S. Pat. No. 4,345,393 is suitable for laminated packaging material comprised of a relatively rigid paperboard or cardboard inner ply, it is not suitable for packaging material having a corrugated inner ply. Since corrugated material, unlike relatively rigid paperboard or cardboard, is subject to crushing, it is not feasible to die cut a perforated tear outline in the outer ply of laminated corrugated packaging material subsequent to lamination. In fact, for this same reason final die cutting and creasing of laminated corrugated packaging material must be performed from the inner ply side rather than the outer ply side in order to avoid crushing of the corrugated flutes.

Thus, despite the existence of detachable coupons for laminated packaging material generally, there remains a need for a coupon which can be detachably incorporated into an outer ply of laminated corrugated packaging material.

SUMMARY OF THE INVENTION

Accordingly, the present invention has been developed to overcome the foregoing shortcomings of existing detachable coupons and the like.

It is therefore an object of the present invention to provide a coupon or the like for incorporation in the outer ply of laminated corrugated packaging material which may be detached without destroying the integrity of the packaging material.

It is yet another object of the present invention to provide a method of manufacturing laminated corrugated packaging material with an incorporated coupon or the like which may be detached without destroying the integrity of the packaging material.

Thus, in accordance with one aspect of the present invention, the shortcomings of existing detachable coupons are overcome by a laminated packaging material comprising a corrugated inner ply; an outer ply having a portion outlined with a perforated die cut; means between facing surfaces of the outer ply and the corrugated inner ply for adhering the facing surfaces to one another; and means on a portion of the facing surface of the outer ply within the perforated die cut outline for preventing adhesion of the portion within the perforated die cut outline to the corrugated inner ply.

In accordance with another aspect of the present invention, the shortcomings of existing detachable coupons are overcome by a process for manufacturing laminated packaging material comprising the steps of applying means to a surface of a portion of an outer ply for preventing adhesion; subsequently outlining the portion of the outer ply coated with the adhesion-preventing means with a perforated die cut; subsequently applying means for bonding only to a facing surface of a corrugated inner ply; and subsequently pressing the facing surface of the corrugated inner ply and a facing surface of the outer ply which includes the adhesion-preventing means together to adhere all of the facing surface of the outer ply, with the exception of the portion within the perforated die cut outline, to the facing surface of the corrugated inner ply.

In accordance with yet another aspect of the present invention, the shortcomings of existing detachable coupons are overcome by a process for manufacturing laminated packaging material comprising the steps of outlining a portion of an outer ply with a perforated die cut; subsequently applying means to a surface of the portion within the perforated die cut outline for preventing adhesion; applying means for bonding to at least one of a facing surface of a corrugated inner ply and a facing surface of the outer ply which includes the adhesion-preventing means; and pressing the facing surfaces of the corrugated inner ply and the outer ply together to adhere all of the facing surface of the outer ply, with the exception of the portion within the perforated die cut outline, to the facing surface of the corrugated inner ply.

In accordance with still other aspects of the present invention, at least the exterior surface of the outer ply, including the portion within the perforated die cut outline, has printed matter thereon, and the portion within the perforated die cut outline comprises a detachable coupon.

In accordance with yet still other aspects of the present invention, means are provided for facilitating removal of the portion within the perforated die cut outline, the facilitating means comprising a slot along the perforated die cut outline and/or a tab on the portion within the perforated die cut outline.

In accordance with still further aspects of the present invention, the adhering means comprises adhesive, the adhesion-preventing means comprises a non-adhering coating, and the nonadhering coating comprises a wax loaded vehicle.

In accordance with yet still a further aspect of the present invention, the corrugated inner ply and the outer ply are together die cut into a predetermined shape for producing a carton, with the portion within the perforated die cut outline at a predetermined location on the carton.

These and other aspects and advantages of the present invention are described in or apparent from the following detailed description of the preferred embodiments.

BRIEF DESCRIPTION OF THE DRAWINGS

The preferred embodiments are described with reference to the drawings in which.

DESCRIPTION OF THE PREFERRED EMBODIMENTS

A laminated corrugated packaging material with detachable coupon in accordance with the present invention will now be described.

Figure 1:
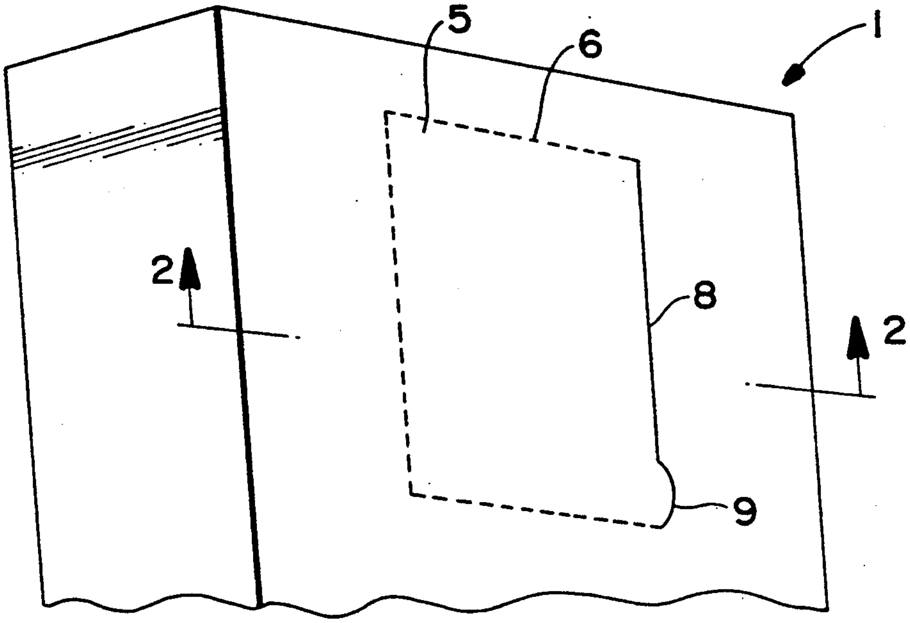
FIG. 1 is a perspective view of a laminated corrugated carton incorporating the detachable coupon of the present invention.
Figure 2:
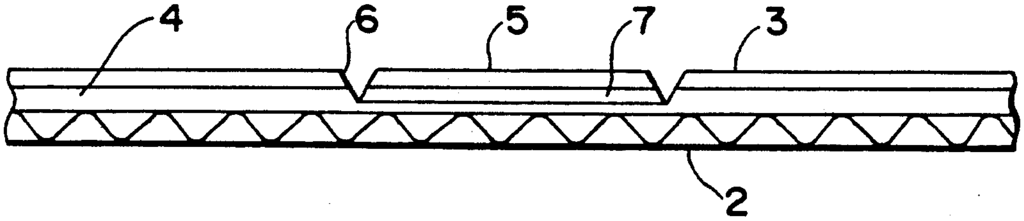
FIG. 2 is an enlarged cross-sectional view taken along line 2—2 of FIG. 1.
Figure 3A:
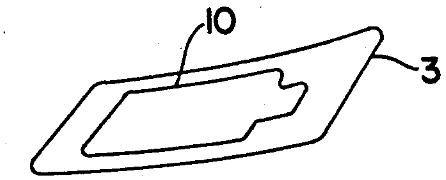
FIGS. 3A-3F are perspective views of the laminated corrugated packaging material with detachable coupon of the present invention at various stages of manufacture.
Figure 3B:
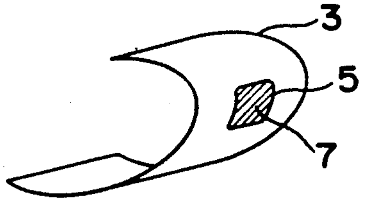
Figure 3C:
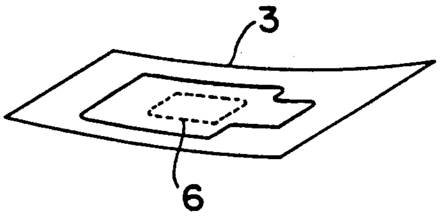
Figure 3D:
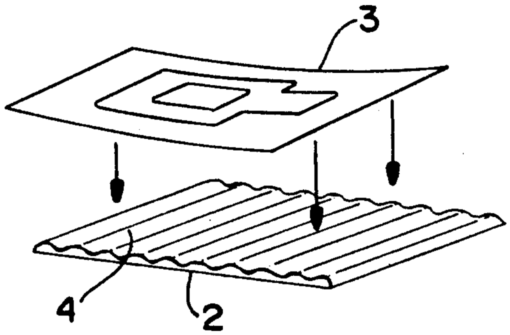
Figure 3E:
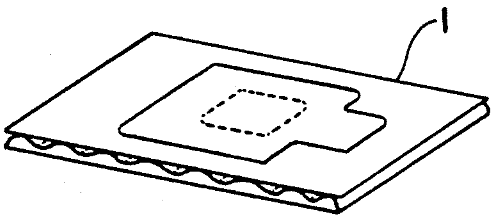
Figure 3F:
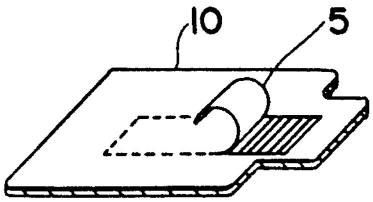

As depicted in FIGS. 1 and 2, a laminated packaging material or carton 1 includes an inner ply 2 formed of a corrugated material, and an outer ply 3 formed of a material suitable for imprinting with art work and identifying information, preferably paperboard. The outer ply 3 is adhesively joined to the inner ply 2 by means of an intervening adhesive layer 4.

A detachable coupon portion 5 is integrally incorporated into a portion of outer ply 3. The coupon portion is defined by a perforated die cut outline 6 extending through outer ply 3 and part of the adhesive layer 4. To permit detachment of coupon portion 5 without destruction of the integrity of the packaging material or carton 1, an adhesion-preventing agent 7 is disposed between a rear surface of the coupon portion and adhesive layer 4. Adhesion-preventing agent 7 prevents adhesion between the rear surface of coupon 5 and adhesive layer 4. The adhesive layer 4 may be dextrin or some other appropriate conventional adhesive. The adhesion-preventing agent may be of any type designed to prevent adhesion to the particular adhesive material employed in adhesive layer 4, such as for example offset varnish or some other wax loaded vehicle. The adhesion-preventing agent 7 preferably is disposed substantially coextensively within perforated die cut outline 6, but may extend beyond perforated die cut outline 6 to a minor extent.

In order to facilitate removal of detachable coupon 5, a long slot 8 may be provided along all or a portion of one side of the perforated die cut outline to permit a knife, letter opener or fingernail to be engaged thereunder. A protruding tab 9 may also be provided along die cut outline 6, preferably along slot 8, to facilitate gripping of detachable coupon 5.

FIG. 3 depicts the various stages for manufacturing the laminated corrugated packaging material with detachable coupon of the present invention. As shown in FIG. 3A, the exterior surface of a paperboard outer ply 3 is initially imprinted with desired decorations, merchandise identification information and redeemable coupon information in the area 10 of the ultimate packaging material. As depicted in FIG. 3B, the reverse side of the paperboard outer ply is then imprinted as necessary (such as, for example, in the area of the redeemable coupon) and the reverse side of the redeemable coupon is coated with the adhesion-preventing agent 7 described above. As shown in FIG. 3C, the area of the packaging material to be encompassed by the redeemable coupon 5 is then outlined with a perforated die cut 6. As depicted in FIG. 3D, an adhesive 4 is then applied to the crests of the corrugated flutes of a facing surface of a corrugated substrate 2, and the paperboard outer ply and corrugated inner ply are then pressed together to form the laminated packaging material 1 depicted in FIG. 3E. Finally, as depicted in FIG. 3F, the laminated packaging material is subsequently die cut to the proper shape 10 designed for assembly into the finished carton or other packaging container. As so manufactured, redeemable coupon 5 is now readily detachable from the finished carton or container without damaging the integrity of the carton or container.

As noted from the foregoing discussion of FIGS. 3A through 3F, it is preferable to first apply the adhesion-preventing agent to the reverse side of the redeemable coupon and then outline the redeemable coupon with the perforated die cut. Since adhesive is only applied to the crests of the corrugated flutes, migration of adhesive into die cut outline 6 is not a problem. However, the die cut outline 6 alternatively may be performed before applying adhesion-preventing agent 7.

Figure 4:
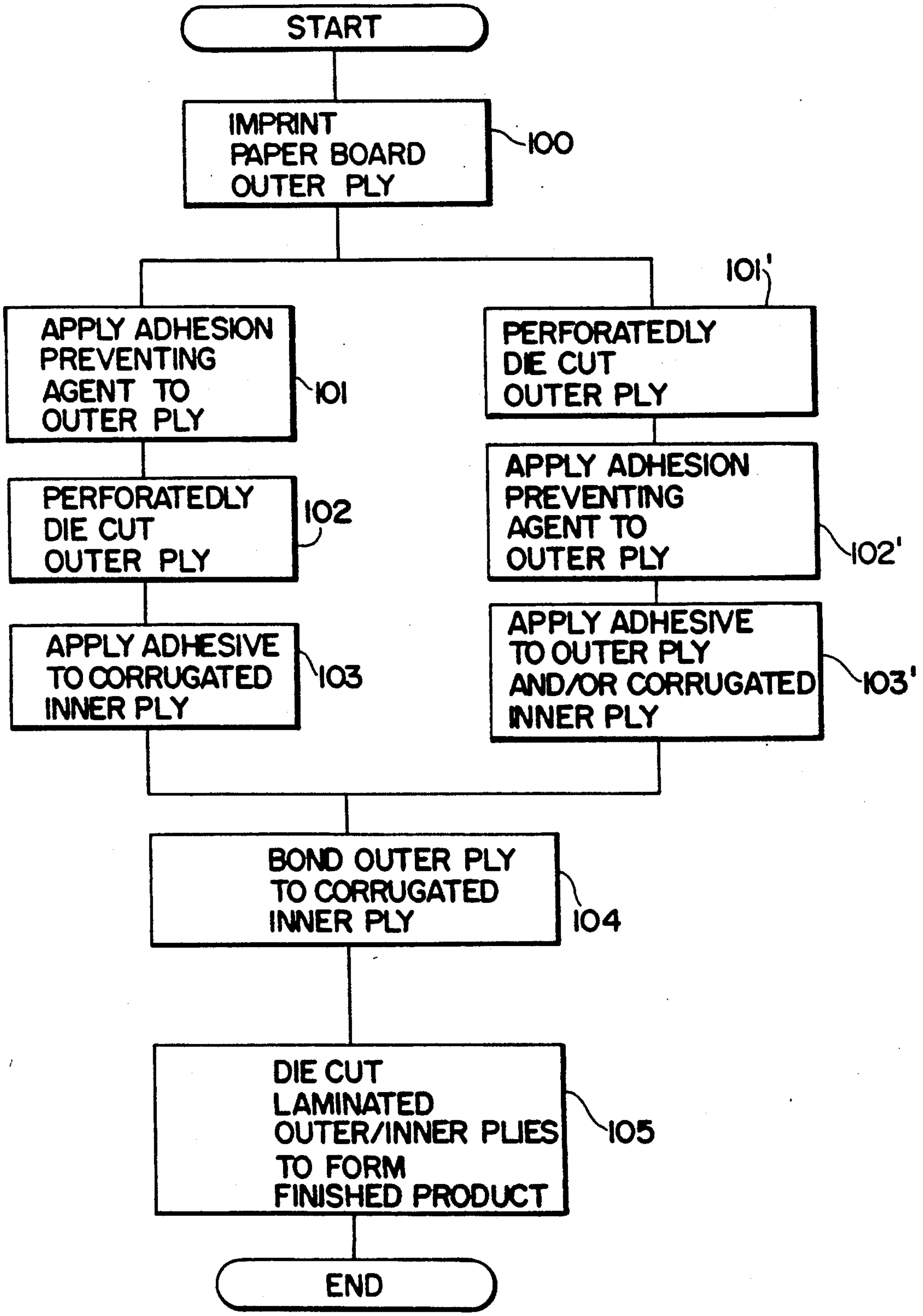
FIG. 4 is a flow chart of the manufacture of the laminated corrugated packaging material with detachable coupon of the present invention.

FIG. 4 displays in flow chart form steps 100 through 105 corresponding to the steps described above with reference to FIGS. 3A-3F. FIG. 4 also depicts alternative steps 101′ through 103′. In this alternative manufacturing mode, a perforated die cut outline is first provided through the paperboard outer ply around the redeemable coupon, and the adhesion-preventing agent is then subsequently applied to the reverse side of the paper-board outer ply in the area of the redeemable coupon (steps 101′ and 102′). With this alternative sequence, adhesion-preventing agent can be applied to the perforated die cut outline itself to ensure that adhesive does not enter the perforated die cut outline and thereby make it difficult to remove the redeemable coupon. Accordingly, in this alternative manufacturing sequence adhesive may be applied to either or both of the facing surfaces of the paperboard outer ply or corrugated inner ply (step 103′).

Figure 5:
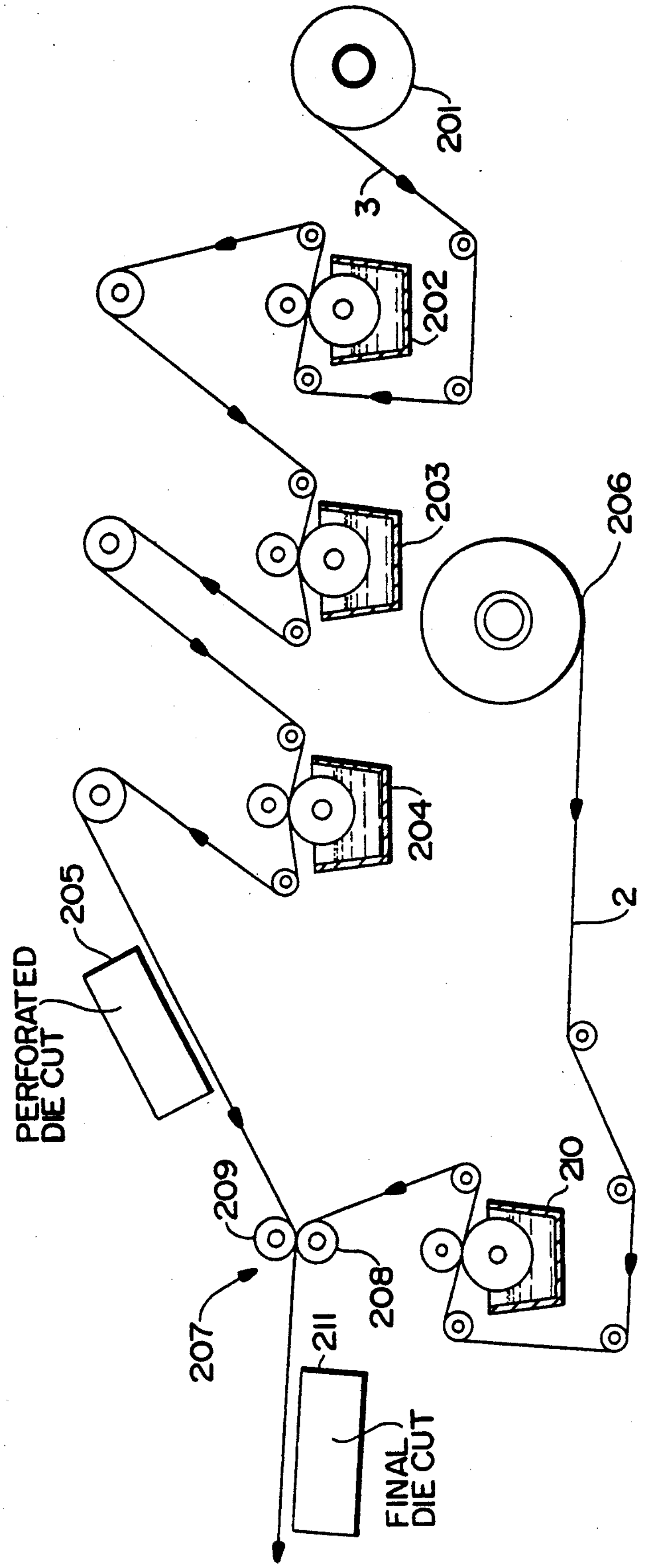
FIG. 5 is a schematic diagram of an assembly line for manufacturing the laminated corrugated packaging material with detachable coupon of the present invention.

FIG. 5 illustrates schematically an assembly line for manufacturing the laminated corrugated packaging material with detachable coupon of the present invention. As shown, paperboard outer ply 3 is fed from a supply spool or source 201, and is directed by means of suitably located rollers through two printing stations 202 and 203, an adhesion-preventing agent applying station 204, and a perforated die cut station 205. Each printing station and the adhesion-preventing agent applying station includes conventional printing apparatus, such as for example a container of printing media, a printing cylinder, a cooperating impression roller and a drying chamber. The perforated die cut station includes conventional cutting apparatus, including for example rotary cutting wheels or a flat bed cutting mechanism.

At the first print station 202, the exterior surface of the paperboard outer ply 3 is imprinted with desired decorations, merchandise identifying information and the redeemable coupon information. At printing station 203, the reverse side of paperboard outer ply 3 is imprinted with any desired decorations or information, including for example the information on the reverse side of the redeemable coupon. Of course, printing station 203 may be omitted if it is not necessary to imprint the reverse side of paperboard outer ply 3.

The adhesion-preventing agent is then applied to the reverse side of the redeemable coupon at adhesion-preventing agent applying station 204, and the perforated die cut outline around the redeemable coupon is then applied through paperboard outer ply 3 at perforated die cut station 205. As described above, the sequence of stations 204 and 205 depicted in FIG. 5 is preferred, but may be reversed.

Paperboard outer ply 3 is then laminated with a corrugated substrate 2 from a supply spool or source 206 at a pressing station 207 comprised of pressing rollers 208, 209. To achieve bonding of paperboard outer ply 3 to corrugated substrate 2, an adhesive is applied to the crests of the flutes of corrugated substrate 2 at adhesive applying station 210. Adhesive applying station 210 includes conventional adhesive applying apparatus, such as for example an adhesive container, an adhesive applicating cylinder and a corresponding impression roller. If the alternating manufacturing steps 101′ through 103′ of FIG. 4 are followed, adhesive applying station 210 may be moved between perforated die cut station 205 and pressing station 207 or an additional adhesive applying station may be added at that location. In any event, at pressing station 207, paperboard outer ply 3 and corrugated substrate 2 become firmly laminated to one another over their entire facing surfaces, with the exception of the area of the redeemable coupon to which the adhesion-preventing agent has been applied.

Finally, the resulting laminated packaging material 1 is die cut into a desired shape at a final die cut station 211. The final die cut station again includes conventional cutting apparatus, such as for example rotary or flat bed cutters.

Obviously, many modifications and variations to the disclosed laminated corrugated packaging material with detachable coupon are possible in light of the above teachings. For example, although the FIG. 5 schematic depicts an assembly line for one color printing, additional printing stations could be provided for multicolor printing of the exterior surface of the paperboard outer ply. Additionally, although the FIG. 5 schematic depicts all of the assembly steps in a single assembly line, it is also possible to separate certain of the assembly steps. For example, it may be preferable to imprint, coat and perforatedly die cut paperboard outer ply 3 on one manufacturing line, while laminating the paperboard outer ply to the corrugated substrate and performing the final die cutting operation on an independent manufacturing line.

In accordance with the above, a laminated corrugated packaging material is provided with a coupon that may be easily detached without destroying the integrity of the packaging material. The laminated corrugated packaging material with detachable coupon may be manufactured in an efficient and cost effective manner.

It is therefore to be understood that, within the scope of the appended claims, the invention may be practiced otherwise than as specifically described. For example, the various aspects of the invention may be selected for combination in a number of permutations other than those shown and described. Thus, while only certain embodiments of the invention have been specifically described herein, it will be apparent that numerous modifications may be made thereto without departing from the spirit and scope of the invention.

What is claimed is:

1. A laminated packaging material comprising:

a corrugated inner ply;

an outer ply having a portion outlined with a perforated die cut;

means between an inner surface of said outer ply and a surface of said corrugated inner ply for fixedly adhering said outer ply and said corrugated inner ply to one another; and means on said inner surface of said outer ply within said perforated die cut outline portion for preventing the fixed adhesion of said outer ply within said perforated die cut outline to said corrugated inner ply to permit the removal of said perforated die cut outline portion of said outer ply without damage to said corrugated inner ply, said perforated die cut outline portion and a remainder of said outer ply outside the perforated die cut outline.

2. The laminated packaging material of claim 1, at least an exterior surface of said outer ply, including said portion within said perforated die cut outline, having printed matter thereon.

3. The laminated packaging material of claim 2, said portion within said perforated die cut outline comprising a detachable coupon.

4. The laminated packaging material of claim 1, further comprising means for facilitating removal of said portion within said perforated die cut outline.

5. The laminated packaging material of claim 4, said removal facilitating means comprising a slot along said perforated die cut outline.

6. The laminated packaging material of claim 5, said removal facilitating means further comprising a tab on said portion within said perforated die cut outline along said slot.

7. The laminated packaging material of claim 1, said adhering means comprising adhesive.

8. The laminated packaging material of claim 1, said adhesion-preventing means comprising a non-adhering coating.

9. The laminated packaging material of claim 8, said non-adhering coating comprising a wax loaded vehicle.

10. The laminated packaging material of claim 1, said adhered outer ply and corrugated inner ply being together die cut into a predetermined shape for producing a carton, with said portion within said perforated die cut outline at a predetermined location on the carton.

* * * * *